United States Patent
Bishop

(10) Patent No.: US 6,558,376 B2
(45) Date of Patent: May 6, 2003

(54) METHOD OF USE OF AN ULTRASONIC CLAMP AND COAGULATION APPARATUS WITH TISSUE SUPPORT SURFACE

(76) Inventor: Gregory D. Bishop, 6103 Glennsbury Ct., West Chester, OH (US) 45069

(*) Notice: Subject to any disclaimer, the term of this patent is extended or adjusted under 35 U.S.C. 154(b) by 56 days.

(21) Appl. No.: 09/888,673

(22) Filed: Jun. 25, 2001

(65) Prior Publication Data

US 2002/0002379 A1 Jan. 3, 2002

Related U.S. Application Data

(60) Provisional application No. 60/215,554, filed on Jun. 30, 2000.

(51) Int. Cl.[7] .............................................. A61B 18/18
(52) U.S. Cl. ........................ 606/27; 606/169; 606/205; 604/22
(58) Field of Search ......................... 606/27, 28, 169, 606/205, 206, 207; 601/2; 604/22

(56) References Cited

U.S. PATENT DOCUMENTS

| | | | |
|---|---|---|---|
| 5,322,055 A | | 6/1994 | Davison et al. |
| 5,908,149 A | | 6/1999 | Welch et al. |
| 6,004,335 A | | 12/1999 | Vaitekunas et al. |
| 6,066,151 A | * | 5/2000 | Miyawaki et al. ............ 606/169 |
| 6,254,623 B1 | * | 7/2001 | Haibel et al. .................. 604/22 |
| 6,340,352 B1 | * | 1/2002 | Okada et al. ................... 601/2 |
| 6,358,264 B2 | * | 3/2002 | Banko ........................ 606/169 |
| 6,425,907 B1 | * | 7/2002 | Shibata et al. ............... 606/169 |
| 6,443,968 B1 | * | 9/2002 | Holthaus et al. ............ 606/169 |

FOREIGN PATENT DOCUMENTS

| | | |
|---|---|---|
| JP | 8-275951 | 10/1996 |
| JP | 9-253088 | 9/1997 |
| WO | WO92/06641 A1 | 4/1992 |

\* cited by examiner

*Primary Examiner*—Michael Peffley
(74) *Attorney, Agent, or Firm*—Verne E. Kreger, Jr.

(57) ABSTRACT

A surgical method for increasing the size of a tissue weld in clamped tissue is disclosed. The method includes providing an end effector for an ultrasonic surgical instrument. The end effector includes an ultrasonic blade having a proximal and a distal end and a clamping mechanism having a clamping surface positioned opposite the ultrasonic blade. The clamping mechanism is adapted to clamp tissue against a side of the ultrasonic blade. A first and a second support surface are positioned laterally on two sides of the ultrasonic blade. Both support surfaces are ultrasonically isolated from the blade and positioned opposite at least a portion of the clamping surface. The method includes actuating the clamping mechanism to clamp tissue between the clamping surface and the ultrasonic blade and between the clamping surface and the first and second tissue support surfaces to define a substantially continuous pressure region. Finally, ultrasonic energy is applied to the ultrasonic blade for the creation of a tissue weld in the substantially continuous pressure region. The tissue weld spreading from tissue clamped between the clamping surface and the ultrasonic blade and into tissue clamped between the clamping surface and the first and second tissue support surfaces.

19 Claims, 11 Drawing Sheets

METHOD OF USE OF AN ULTRASONIC CLAMP AND COAGULATION APPARATUS WITH TISSUE SUPPORT SURFACE

This application claims the benefit of Provisional application Ser. No. 60/215,554, filed Jun. 30, 2000.

FIELD OF THE INVENTION

The present invention relates, in general, to ultrasonic surgical devices and, more particularly, to a new ultrasonic surgical instrument and method including inactive tissue clamping surfaces positioned laterally on either side of a longitudinal ultrasonic blade.

BACKGROUND OF THE INVENTION

Ultrasonic surgical instruments are continuing to gain acceptance with surgeons as a replacement for a variety of conventional surgical instruments. The advantages of a single instrument that uses ultrasonic energy for cutting, coagulating, or welding tissue is of great value to the surgical community. Applying ultrasonic vibrational energy to tissue is rapid, results in minimal trauma and bleeding, and is sometimes referred to as "bloodless surgery".

An elongated blade extends from the distal end of the ultrasonic surgical instrument and is ultrasonically vibrated to a resonance condition by a transducer assembly. Pressing the exposed vibrating blade against tissue transmits ultrasonic energy to the tissue. Due to the ultrasonic vibrations, a distal portion of the elongated blade oscillates rapidly in a proximal to distal manner relative to the longitudinal axis of the instrument. This rapid oscillation or proximal to distal movement of the elongated blade is known as excursion. Excursion is non-uniform along the exposed blade length, attaining a maximum at the distal end and decreasing toward the proximal portion of the exposed blade. Tissue effects are directly related to the excursion of the elongated blade, with the greatest tissue effects being obtained at or near to the distal end. Application of the distal end to tissue results in cavitation effects such as coagulation and emulsification, and the sides of the blade produce frictional effects such as coagulation and cutting.

Three elements control the tissue coagulation effects: pressure applied to the tissue by the active blade (i.e.: force), the amount of energy delivered to the tissue by the blade (i.e.: power), and the duration of the energy delivery (i.e.: time). Different tissue effects are obtained by varying these parameters and by using different portions of the elongated ultrasonic blade on tissue. Placing the side of the elongated blade against tissue produces a frictional interaction between the elongated blade member and the tissue. This frictional interaction creates heat within the tissue and coagulates tissue adjacent to the oscillating elongated blade. Continued application of energy to tissue (with the side of the blade) produces a tissue coagulation zone, which spreads away from the elongated blade producing an effect known as lateral thermal spread. Using the sides of the blade to cause lateral thermal spread has proven useful when hemostatically sealing vessels or welding portions of tissues together.

Clamping or compressing tissue together prior to the application of energy was found to facilitate the sealing and welding process. Good tissue welds are obtained by applying a combination of pressure and energy to a selected portion of tissue. First, tissue is clamped or compressed together into a desired tissue orientation and second, ultrasonic energy is applied to the compressed tissue to weld it together. Combining a clamping mechanism with the elongated blade ultrasonic instrument proved revolutionary with the surgical community.

One type of ultrasonic surgical instrument clamps tissue directly against the side of the elongated blade. This type of a clamp and coagulation instrument generally has a clamp arm that is moveable from a first position spaced away from the side of the blade to a second position clamped against the side of the elongated blade. Clamping tissue against the side of the elongated blade increases the transfer of energy to tissue and enhances tissue coagulation and cutting effects. Additionally, using the side of the elongated blade provides the surgeon with a large tissue bite. Examples of ultrasonic surgical instruments that clamp against the side of the blade are described in the U.S. Pat. No. 5,322,055 by Davison et al., and in a Japanese Laid-Open Patent Application (Kokai) No. 8-275951 by Mitsumasa Okada et al.

Another type of ultrasonic instrument uses the distal end of the elongated blade to cut, and has a tissue clamping mechanism spaced distally away from the elongated blade. The ultrasonic instrument has a pair of opposed jaws that are moveable from an open position to a closed position for compressing tissue therebetween. A central passageway extends longitudinally within the closed jaws for the passage of the elongated blade, and tissue is compressed laterally on either side of the advancing elongated blade. Examples of these types of ultrasonic surgical instruments can be found in U.S. patent application Ser. No. 6,004,335 by Vaitekunas et al. and in Japanese Unexamined Patent Application No. 9-253088 by Makoto Miyawaki et al.

Vaitekunas et al. teaches a surgical ultrasonic instrument that has a pair of flexible jaw members formed from a cantilever spring material. The flexible jaw members clamp upon tissue and are opened and closed by a conventional tube closure mechanism. A passageway or longitudinal slot is provided within each of the flexible jaws for the passage of an ultrasonic blade. A flat knife blade forms the distal end of the elongated blade and is aligned with the slots within the flexible jaws. The flat knife blade travels down the slots within the flexible jaw members cutting and coagulating the uncompressed tissue within the longitudinal slot.

The Makoto Miyawaki et al. surgical instrument has a pair of cantilever spring jaw beams extending from the distal end of the ultrasonic surgical instrument with rigid jaws extending from the jaw beams. The cantilever spring jaw beams are formed in a normally deflected open position and are opened and closed by a conventional tube closure mechanism. When closed, the rigid jaws clamp tissue laterally on opposite sides of the advancing blade. A narrow longitudinal passageway is provided between the rigid jaws for passage of the elongated blade.

Advancing the blade through the central within the passageway emulsifies or cuts the uncompressed portion of tissue directly in front of the blade, and coagulates tissue laterally to the moving blade. However, there is little lateral spread with these types of instruments and consequently, a narrow coagulation zone or tissue weld zone.

Tissue weld strength depends on two factors: compressing or clamping tissue at the weld site, and the surface area or size of the weld. Compressing the tissue sample before welding ensures the clamped tissue is homogeneous and all portions of the tissue are held in the desired configuration as the energy is applied. Assuming the tissue is properly compressed during welding, tissue weld strength will directly depend on surface area, i.e.: twice the weld area, twice the strength. Using the distal end of a blade member to cut and coagulate uncompressed tissue produces a narrow coagulation zone in uncompressed tissue, and a small tissue weld area.

Ultrasonic surgical instruments that use the side of the elongated blade to clamp produce a wide coagulation zone (caused by lateral thermal spread), however they lack the ability to clamp tissue laterally to the elongated blade. This reduces the potential strength of the tissue weld as portions of the coagulated tissue lie outside of the compressed tissue area, i.e.: outside of the tissue clamped between the clamp arm and the blade. Thus, tissue coagulated outside of the compressed tissue area is coagulated in an uncompressed condition, and weld strength suffers.

What is needed is an ultrasonic clamp and coagulation instrument that offers the advantages of all of the above ultrasonic surgical instruments by producing a wide tissue weld in compressed or clamped tissue. Therefore it would be advantageous to provide an ultrasonic surgical instrument that provides a substantially continuous pressure region that extends laterally on either side of the elongated blade member as well as against the side of the blade member, and can weld this substantially continuous pressure region with lateral thermal spread. Thus, this ultrasonic instrument can increase the size of the tissue weld by using lateral thermal spread to spread or expand the weld into adjacent compressed tissue, and into compressed tissue that is spaced laterally away from the elongated blade. In comparison, Vaitekunas et al. and Makoto Miyawaki et al. provide a non-continuous pressure region. They compress tissue laterally to both sides of the elongated blade, and provide uncompressed tissue in the path of the advancing elongated blade. Additionally, Vaitekunas et al. and Makoto Miyawaki et al. use the distal end of the elongated blade. This produces minimal coagulation or thermal effects in the uncompressed tissue and little or no effects to the laterally compressed tissue. Presently, there are no known ultrasonic surgical instruments or methods of use of such an instrument that can provide the surgeon with the improvements and benefits described above.

SUMMARY OF THE INVENTION

The present invention is a novel surgical method for increasing the size of a tissue weld in clamped tissue. The method, according to the present invention includes providing an end effector for an ultrasonic surgical instrument. The end effector includes an ultrasonic blade having a proximal and a distal end and a clamping mechanism having a clamping surface positioned opposite the ultrasonic blade. The clamping mechanism is adapted to clamp tissue against a side of the ultrasonic blade. A first support surface is positioned laterally on a first side of the ultrasonic blade, the first support surface being ultrasonically isolated from the blade and positioned opposite at least a portion of the clamping surface. A second support surface is positioned laterally on a second side of the ultrasonic blade, the second support surface also being ultrasonically isolated from the blade and positioned opposite at least a portion of the clamping surface.

Next, the clamping mechanism is actuated to clamp tissue between the clamping surface and the ultrasonic blade and between the clamping surface and the first and second tissue support surfaces. The clamped tissue defining a substantially continuous pressure region.

Finally, ultrasonic energy is applied to the ultrasonic blade for the creation of a tissue weld in the substantially continuous pressure region. The tissue weld spreads from tissue clamped between the clamping surface and the ultrasonic blade and into tissue clamped between the clamping surface and the first and second tissue support surfaces.

An alternate surgical method for increasing the size of a tissue weld in compressed tissue is disclosed. The alternate method comprises the following steps:

First, providing an end effector for an ultrasonic surgical instrument, the end effector including an ultrasonic blade having a proximal and a distal end and a clamping mechanism having a clamping surface positioned opposite the ultrasonic blade. The clamping mechanism is adapted to clamp tissue against the ultrasonic blade. A first support surface is positioned laterally on a first side of the ultrasonic blade, the first support surface being ultrasonically isolated from the blade and positioned opposite at least a portion of the clamping surface. The first support surface also having a support surface angle relative to the longitudinal axis of the ultrasonic blade. A second support surface is positioned laterally on a second side of the ultrasonic blade, the second support surface being ultrasonically isolated from the blade and positioned opposite at least a portion of the clamping surface. The second support surface also having generally the same support surface angle as the first support surface;

Second, the clamping mechanism is moved to a first position to clamp tissue between the clamping surface and the first and second support surfaces. The clamped tissue is spaced away from the ultrasonic blade and has an uncompressed tissue region positioned opposite the blade.

Third, the clamping mechanism is moved to a second position to clamp the uncompressed tissue region against the ultrasonic blade to create a substantially continuous pressure region within the tissue clamped within the end effector.

Last, applying ultrasonic energy to the clamped tissue in contact with the ultrasonic blade to create a tissue weld, the tissue weld spreading away from the clamped tissue in contact with the ultrasonic blade and into clamped tissue adjacent to and spaced away from the ultrasonic blade.

Additionally, yet another alternate surgical method for increasing the size of a tissue weld in compressed tissue is disclosed. The alternate method comprises the following steps:

First, providing an end effector for an ultrasonic surgical instrument, the end effector including an ultrasonic blade having a proximal and a distal end and a clamping mechanism having a clamping surface positioned opposite the ultrasonic blade. The clamping mechanism is adapted to clamp tissue against the ultrasonic blade. A first support surface positioned laterally on a first side of the ultrasonic blade, the first support surface being ultrasonically isolated from the blade and positioned opposite at least a portion of the clamping surface. The first support surface also has a support surface angle relative to the longitudinal axis of the ultrasonic blade. A second support surface positioned laterally on a second side of the ultrasonic blade, the second support surface being ultrasonically isolated from the blade and positioned opposite at least a portion of the clamping surface. The second support surface has generally the same support surface angle as the first support surface.

Second, the clamping mechanism is moved to a first position to clamp tissue between the clamping surface and the first and second support surfaces. The clamped tissue is spaced away from the ultrasonic blade and the tissue has an uncompressed tissue region opposite the blade.

Third, the ultrasonic blade is activated.

And last, the clamping mechanism is moved to a second position to clamp tissue against the active ultrasonic blade to create a tissue weld within the substantially continuous pressure region.

The various features of novelty which characterize the invention are pointed out with particularity in the claims annexed to and forming a part of the disclosure. For a better understanding of the invention, reference is made to the accompanying drawings and descriptive matter in which the preferred embodiments of the invention are illustrated

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The present invention relates, in general, to a novel ultrasonic surgical instrument for the clamping and coagulation of tissue during a surgical procedure. More particularly, the present invention relates to a method of use of an ultrasonic clamp and coagulation instrument having an improved tissue clamping mechanism that clamps tissue against a side of a longitudinal ultrasonic blade, and has inactive tissue clamping surfaces located laterally on either side of the longitudinal ultrasonic blade.

Figure 1:
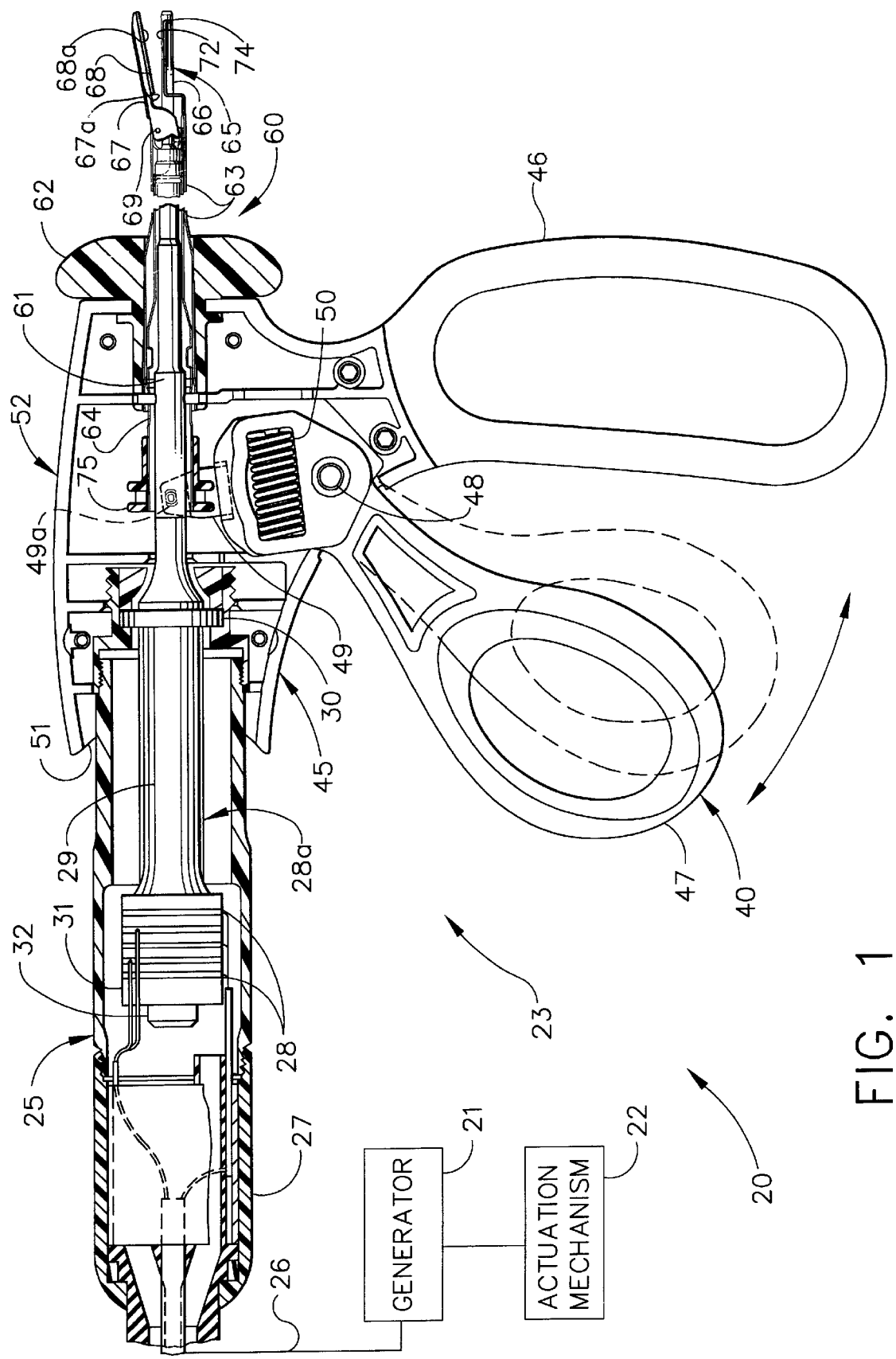
FIG. 1 is a side elevational view of an ultrasonic surgical system wherein an improved surgical instrument of the surgical system is shown in a cross sectional view.
Figure 2:
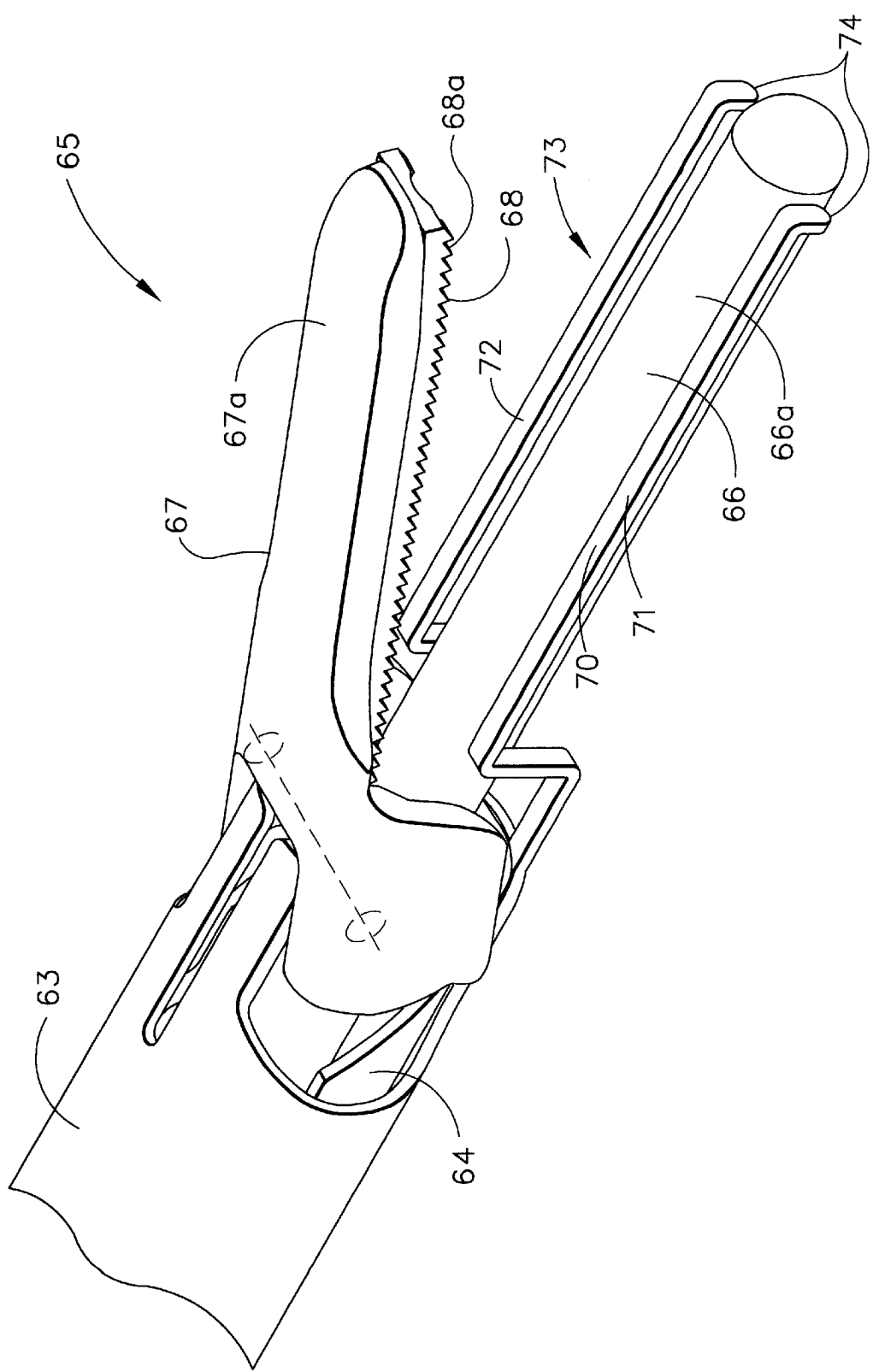
FIG. 2 is an enlarged isometric view of a distal end of the improved surgical instrument of FIG. 1 showing an end effector having a blade, a first and a second support beam, and a moveable clamp arm.

Referring now to FIGS. 1 and 2, the ultrasonic surgical system 20 has an ultrasonic clamp and coagulation instrument henceforth referred to as surgical instrument 23, an ultrasonic generator 21 for the generation of electrical signals, and an operator controlled generator actuation mechanism 22. A cable 26 carries electrical signals from the generator 21 to the surgical instrument 23. The surgical instrument 23 converts the electrical signals from the generator 21 into ultrasonic energy that is transmitted to a distal end effector 65 by a waveguide 61. Ultrasonic energy is delivered to an elongated ultrasonic blade 66 of the end effector 65 at a resonant frequency suitable for the cutting, coagulating, and welding of body tissue. Thus, the ultrasonic blade 66 is an ultrasonic energy source that delivers ultrasonic energy to tissue. The ultrasonic energy may, for example be delivered at a frequency between 20 kHz and 250 kHz, and preferably at a frequency of 55 kHz. A moveable clamping mechanism 67 is located adjacent to the ultrasonic blade 66 for the clamping of tissue against the ultrasonic blade 66. A phase lock loop control system is provided as a part of ultrasonic generator 21 to adjust the frequency of the electrical signals to match the resonant frequency of the surgical instrument 23, and to change the frequency of the electrical signals when the ultrasonic blade 66 is subjected to a tissue load. A second feedback loop is provided as a part of generator 21 to maintain a constant electrical current level to control the excursion or proximal and distal movement of a distal end of the ultrasonic blade 66. Generator actuation mechanism 22 is generally a foot-activated pedal that is used to activate the generator 21. A suitable ultrasonic generator is the GEN01 Ultracision® Generator and a suitable foot pedal is the GEN03 Footswitch, both available from Ethicon Endo-Surgery, 4545 Creek Road, Cincinnati, Ohio The surgical instrument 23 is assembled from two components: an ultrasonic drive unit 25 for converting the electrical signals from the generator 21 into ultrasonic energy, and a handle assembly 45. Handle assembly 45 has the ultrasonic blade 66a at a distal end and the clamping mechanism 67 for the clamping of tissue against the ultrasonic blade 66. Ultrasonic drive unit 25 is removeably mountable within a receptacle 51 at a proximal end of a body 52 of the handle assembly 45. An exterior housing 27 surrounds the ultrasonic drive unit 25 and isolates the components therein. Cable 26 enters a proximal end of the exterior housing 27 and is electrically connected to a stack of piezoelectric elements 28. An acoustic assembly 28a is formed by compressing the stack of piezoelectric elements 28 between a proximal end bell 31 and a distal vibration transmission member 29, and securing the compressed assembly with a bolt 32.

Electrical signals from the generator 21 forces the piezoelectric elements 28 to undergo a rapid series of physical expansions and contractions. These expansions and contractions create a series of mechanical pulses or high frequency longitudinal waves of ultrasonic energy within acoustic assembly 28a. A resilient mount 30 is attached to the vibration transmission member 29 to constrain the acoustic assembly 28a within the exterior housing 27. Mount 30 also vibrationally isolates the acoustic assembly from the exterior housing 27. The assembled surgical instrument 23 can be used in an un-powered mode to clamp or grasp tissue, or in a powered mode to coagulate, cut, or weld tissue. An example of a suitable ultrasonic drive unit 25 is the Model No. HP050, which is available from Ethicon Endo-Surgery, 4545 Creek Road, Cincinnati, Ohio. An example of a suitable handle assembly 45 is the LCS-15 also available from Ethicon Endo-Surgery, 4545 Creek Road, Cincinnati, Ohio.

The vibration transmission member 29 of the ultrasonic drive unit 25 removeably and operably couples to a waveguide 61 of the handle assembly 45 to make the ultrasonic clamp and coagulation apparatus 40. A threaded connection (not shown) removeably and operably connects the vibration transmission member 29 of the ultrasonic drive unit 25 to a waveguide 61 of the handle assembly 45. Waveguide 61 extend distally through the handle assembly 45 from the vibration transmission member 29 to the ultrasonic blade 66 located at the distal end of the waveguide 61. Waveguide 61 is generally made of a material such as aluminum or titanium.

Figure 3:
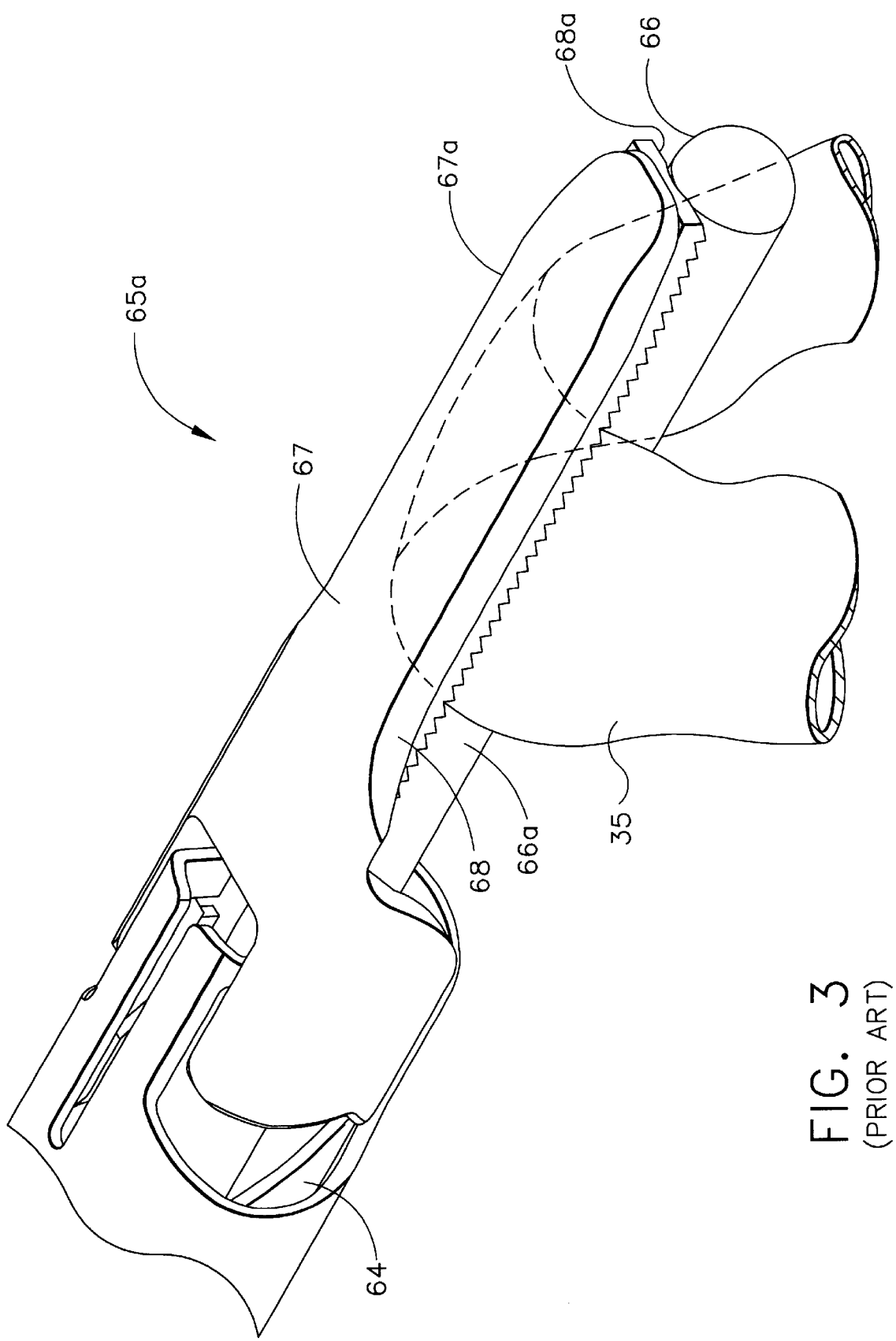
FIG. 3 is an enlarged isometric view of a distal end of a prior art surgical instrument, wherein the end effector has closed upon a vessel.

A shaft assembly 60 rotatably mounts into the body 52 and has an outer sheath 63 surrounding most of the waveguide 61. Outer sheath 63 is an elongated tubular member vibrationally isolated from the waveguide 61 and has clamping mechanism 67 pivotably attached at its distal end. A rotation knob 62 is fixedly attached at the proximal end of outer sheath 63 and rotatably mounts within the body 52. Rotation knob 62 rotates the shaft assembly 60 within the body 52, and around the waveguide 61. Clamping mechanism 67 has a moveable clamp arm 67a extending distally from the outer sheath 63 and adjacent to the ultrasonic blade 66. Clamp arm 67a is pivotably attached (at the proximal end) to the outer sheath 63 by a pivot 69 and is moveable from an open position spaced away from ultrasonic blade 66 (FIGS. 1 and 2) to a closed position adjacent to ultrasonic blade 66 (FIG. 3). Pivot 69 defines a pivot axis about which clamp arm 67a pivots. An actuation member 64 is moveably located between outer sheath 63 and waveguide 61 and is operably coupled to the clamp arm 67a at a distal end. A drive collar 75 is fixedly attached to a proximal end of the actuation member 64 within the body 52. Proximal and distal motion of the drive collar 75 within the body 52 closes and opens the clamping mechanism 67.

A handgrip 46 extends fixedly downward from a distal portion of the body 52 and an operating lever 47 pivotably extends downward from the proximal portion of the body 52. Operating lever 47 pivots about a pivot mount 48 and is operably and rotatably coupled to the drive collar 75 by a drive yoke 49. Drive yoke 49 rotates about the pivot mount 48 and is operably coupled to the operating lever 47 by a force limiting spring 50. An upper portion of the drive yoke 49 is "U" shaped and straddles the waveguide 61 (FIG. 1). A front portion of the drive yoke 49 is sectioned and removed in FIG. 1. A pair of opposed pins 49a extend inwardly within the "U" of drive yoke 49 to engage with a slot of the drive collar 75 (shown sectioned). A pin 49a (non-crosshatched) is shown sectioned in the proper position in the foreground for clarity. Proximal motion of the operating lever 47 opens the clamping mechanism 67 and distal motion of the operating lever 47 (dashed lines, FIG. 1) closes the clamping mechanism 67 against the ultrasonic blade 66. Force limiting spring 50 limits the amount of closure force that can be applied against the ultrasonic blade 66.

Figure 7:
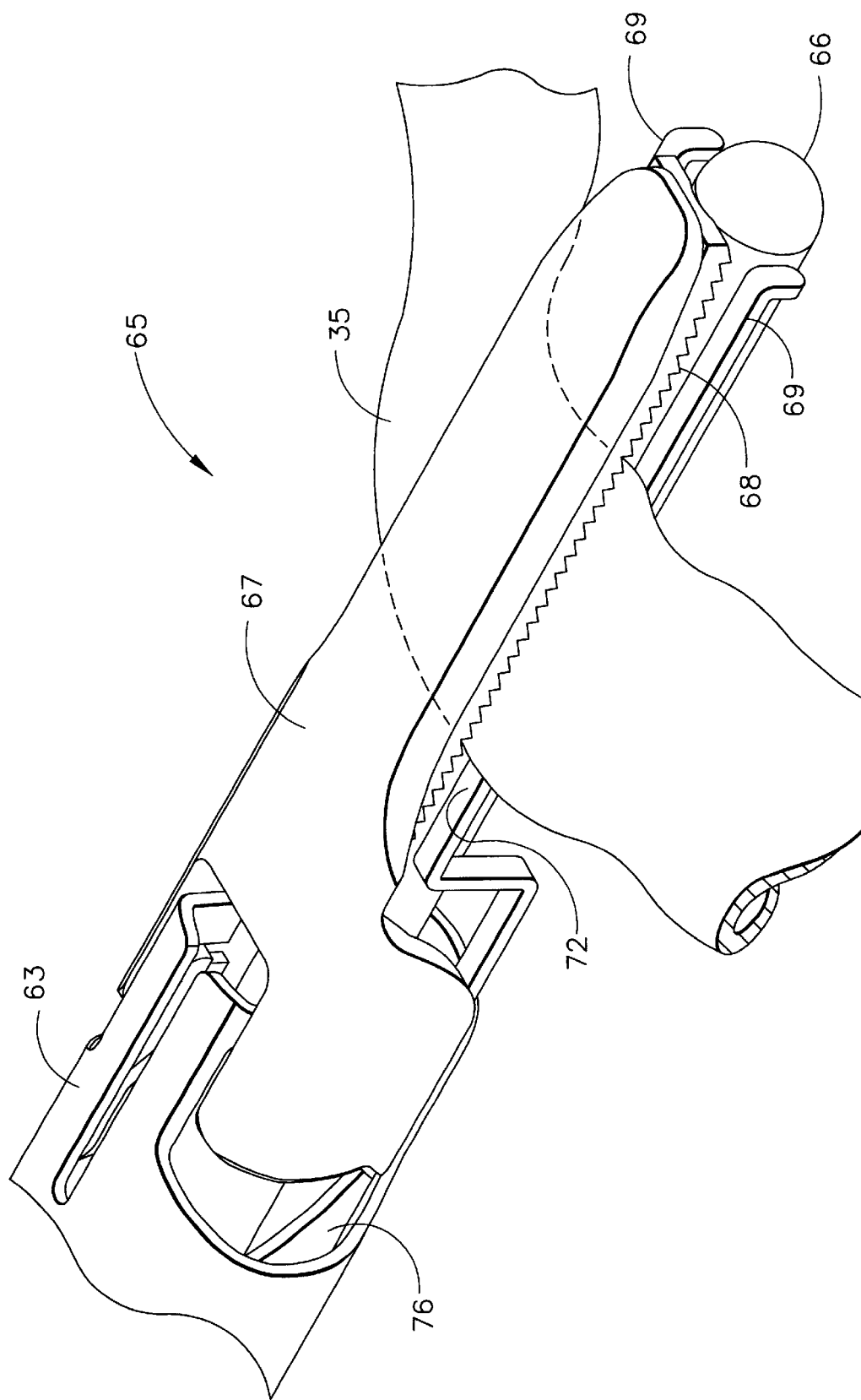
FIG. 7 is an enlarged isometric view of the improved surgical instrument of FIG. 2, wherein the end effector has closed upon a vessel.

FIG. 2 is an enlarged view of the end effector 65 which has ultrasonic blade 66 for the delivery of ultrasonic energy to tissue and clamping mechanism 67 for clamping tissue against a blade surface 66a of the ultrasonic blade 66. Clamp arm 67a is shown in the open position for the reception of tissue and is moveable to a closed position to clamp tissue against the ultrasonic blade 66 (FIG. 7). Clamp arm 67a is operatively connected to the actuating member 64, which can be seen within outer sheath 63. A resilient clamp pad 68 is located on the inner side of clamp arm 67a and has a clamping surface 68a facing the ultrasonic blade 66. Clamp pad 68 vibrationally isolates clamp arm 67a from ultrasonic blade 66 when the clamp arm 67a is in the closed position. First and a second support beams 70,72 having a first and a second support surfaces 71,73 respectively, flank the ultrasonic blade 66 on either side. First and second support surfaces 71,73 are ultrasonically isolated, e.g.: not in contact with and spaced away from the ultrasonic blade 66, and extend along the entire length of the treatment region of ultrasonic blade 66 and the clamping surface 68a. Support surfaces 71 and 73 are positioned opposite to and face the clamping surface 68a when clamp arm 67a is in the open position, and contact the clamping surface 68a when the clamp arm 67a is in the closed position. When tissue is positioned within the end effector 65, first and second support surfaces 71, 73 compress or clamp tissue against clamping surface 68a. First and second support beams 70,72 may be cantilever springs. Additionally, first and second support surfaces 71, 73 are positioned parallel to one another such that they are in the same plane with clamp arm 67a open. Support beams 70,72 extend from the metallic outer sheath 63 and may include a blunt distal end 74 to provide an atraumatic tissue contact surface at the distal ends of support beams 70, 72.

FIGS. 3–6 illustrate the prior art end effector 65a, its method of use, and results when used upon tissue such as a vessel 35. Due to the similarities between the prior art device and the preferred invention described above, like components, or nearly identical components, will have the same element numbers and descriptions with components having the same element numbers having the same function. Vessel 35 is shown draped over the ultrasonic blade 66 and clamp arm 67a in a closed position. The effects of applying ultrasonic energy to a vessel 35 in such a draped position will be described below.

Figure 4:
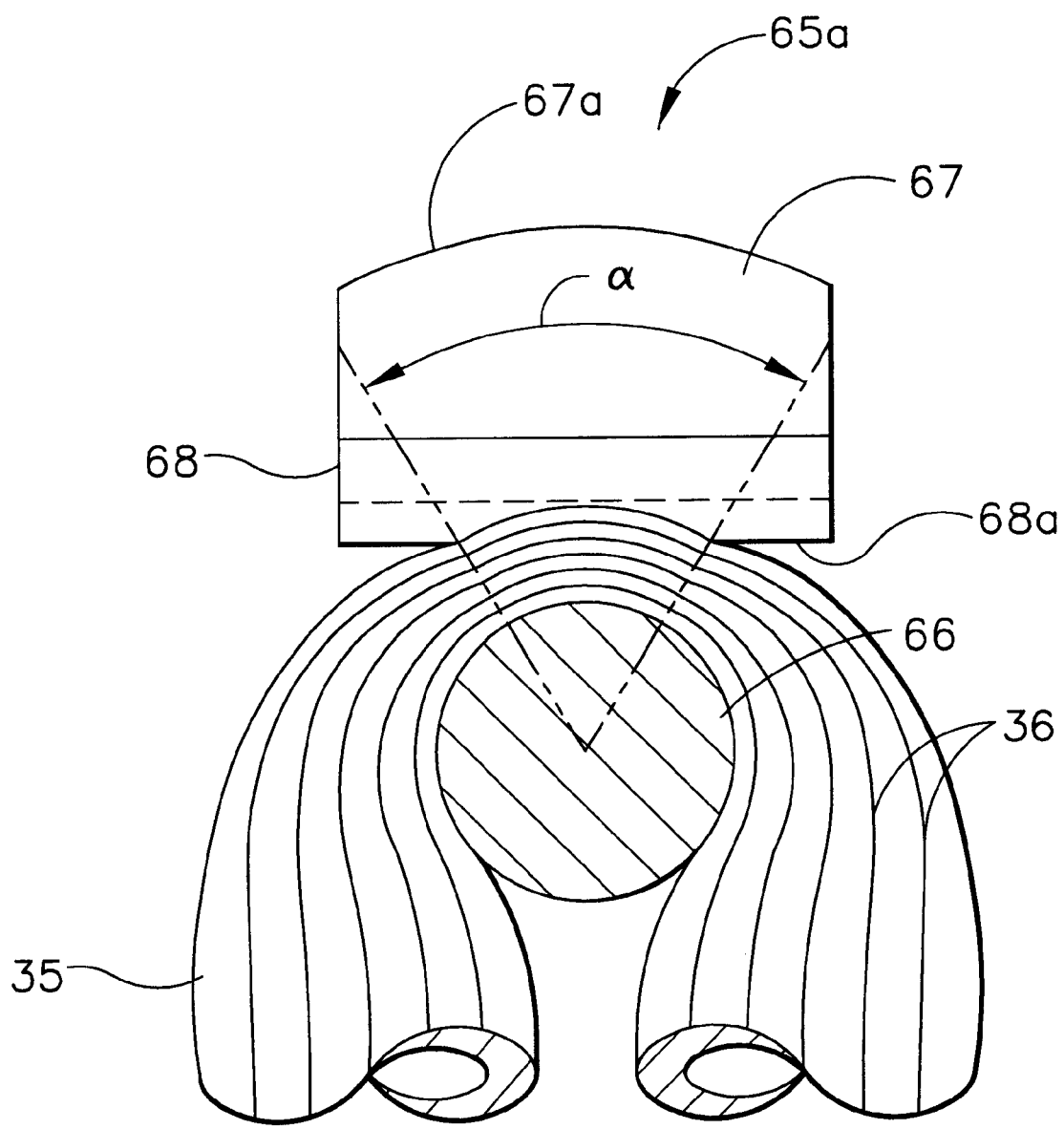
FIG. 4 is an enlarged cross sectional view of the distal end effector of the prior art surgical instrument of FIG. 3, wherein the end effector has closed upon a vessel.

Good hemostasis, coagulation, cutting, or tissue welding depends upon the application of both pressure and energy to tissue or vessels. FIG. 4 is a cross sectional view of the instrument illustrated in FIG. 3 and shows a sectioned end view of the prior art end effector 65a clamped on vessel 35. Pressure is exerted upon the tissue of the vessel 35 by the clamped prior art end effector 65a. A series of pressure streamlines 36 are shown within the vessel 35 to show the effects of pressure on a clamped vessel 35. Pressure streamlines 36 are also used in FIGS. 8, 13, and 14. Spacing between the pressure streamlines 36 varies to indicate areas of higher or lower compression. Closer spacing indicates areas of higher pressure.

As shown, an angular portion of vessel 35 is clamped between the prior art ultrasonic blade 66 and the clamping surface 68a and is defined as a tissue compression zone α. The tissue clamped within the tissue compression zone α has pressure streamlines 36 that are close together to indicate the clamping pressure applied by clamp arm 67a.

Figure 5:
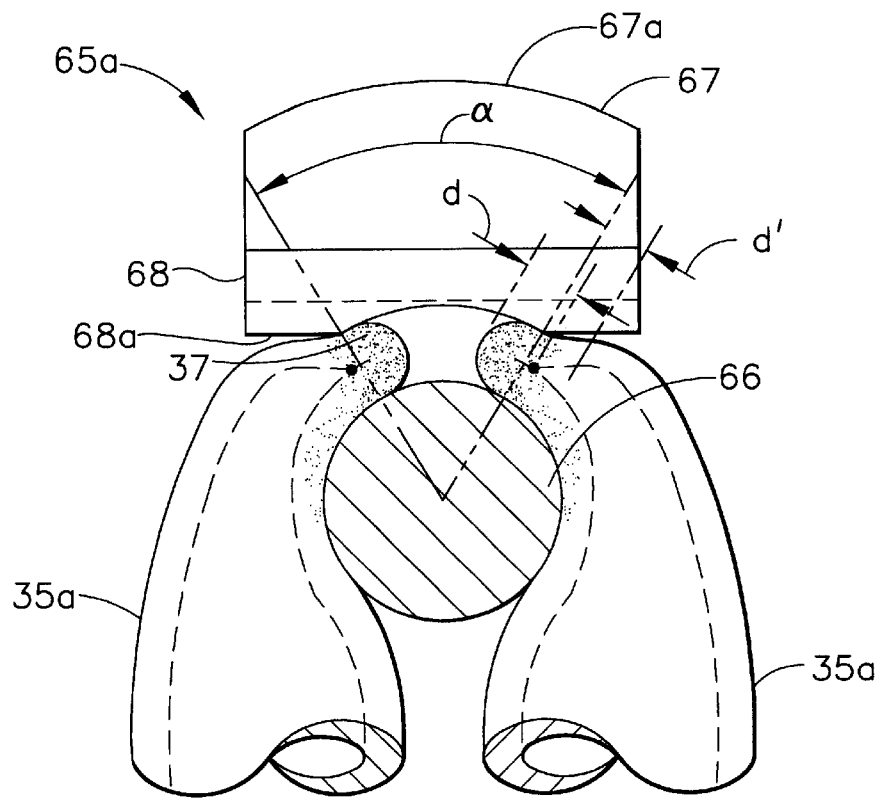
FIG. 5 is an enlarged cross sectional view of the distal end of the prior art surgical instrument of FIG. 4 wherein the application of ultrasonic energy has coagulated and cut the vessel within the end effector.
Figure 6:
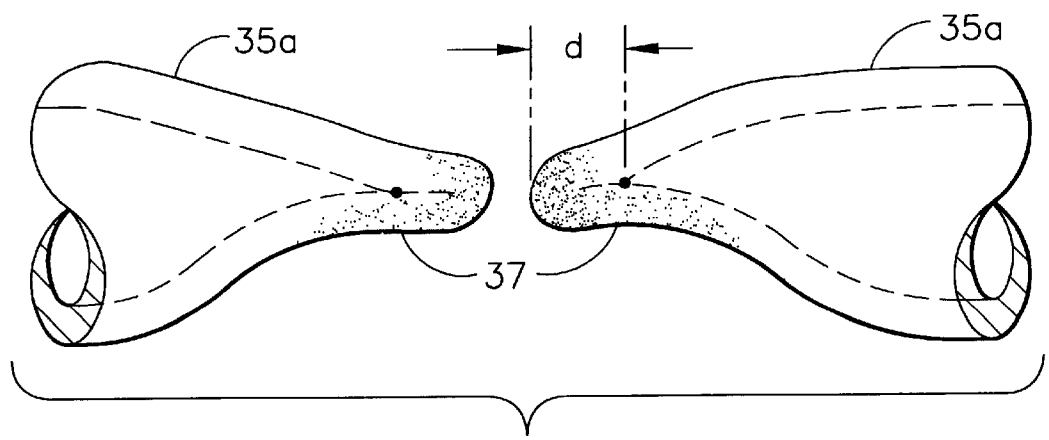
FIG. 6 is an enlarged view of the coagulated and cut vessel of FIG. 5 after release from the prior art surgical instrument, wherein the coagulated tissue is identified by stippling.

In FIGS. 5 and 6, ultrasonic energy has been applied to the clamped vessel 35 by the prior art end effector 65a. The vessel 35 has been cut into a pair of severed vessels 35a and a portion of coagulated tissue 37 can be found at the end of each segment of the severed vessels 35a. Stippling will henceforth be used to identify coagulated tissue. Upon cutting, the severed vessels 35a fall from the closed prior art end effector 65a (FIG. 6). The ends of the severed vessels 35a are composed of two different types of coagulated tissue: tissue compressed and welded together designated by welded tissue length "d", and adjacent coagulated tissue (which is not welded) designated by coagulated tissue length "d'". The welded tissue length "d" is composed primarily of tissue from within the angular tissue compression zone "α" and may include a small amount of additional welded tissue that is adjacent to but slightly beyond the compression zone "α". The coagulated tissue length "d'"is caused by contact of an uncompressed portion of the severed vessel 35a against the ultrasonic blade 66. Since pressure is not applied when this tissue is coagulated, coagulated tissue length "d'" is not welded. Thus, the method of use of the prior art instrument is to compress tissue against the side of the ultrasonic blade 66, and to apply ultrasonic energy to the compressed tissue. The application of ultrasonic energy to compressed tissue creates a tissue weld and lateral thermal spread coagulates uncompressed tissue adjacent to and spaced away from the ultrasonic blade 66.

Figure 8:
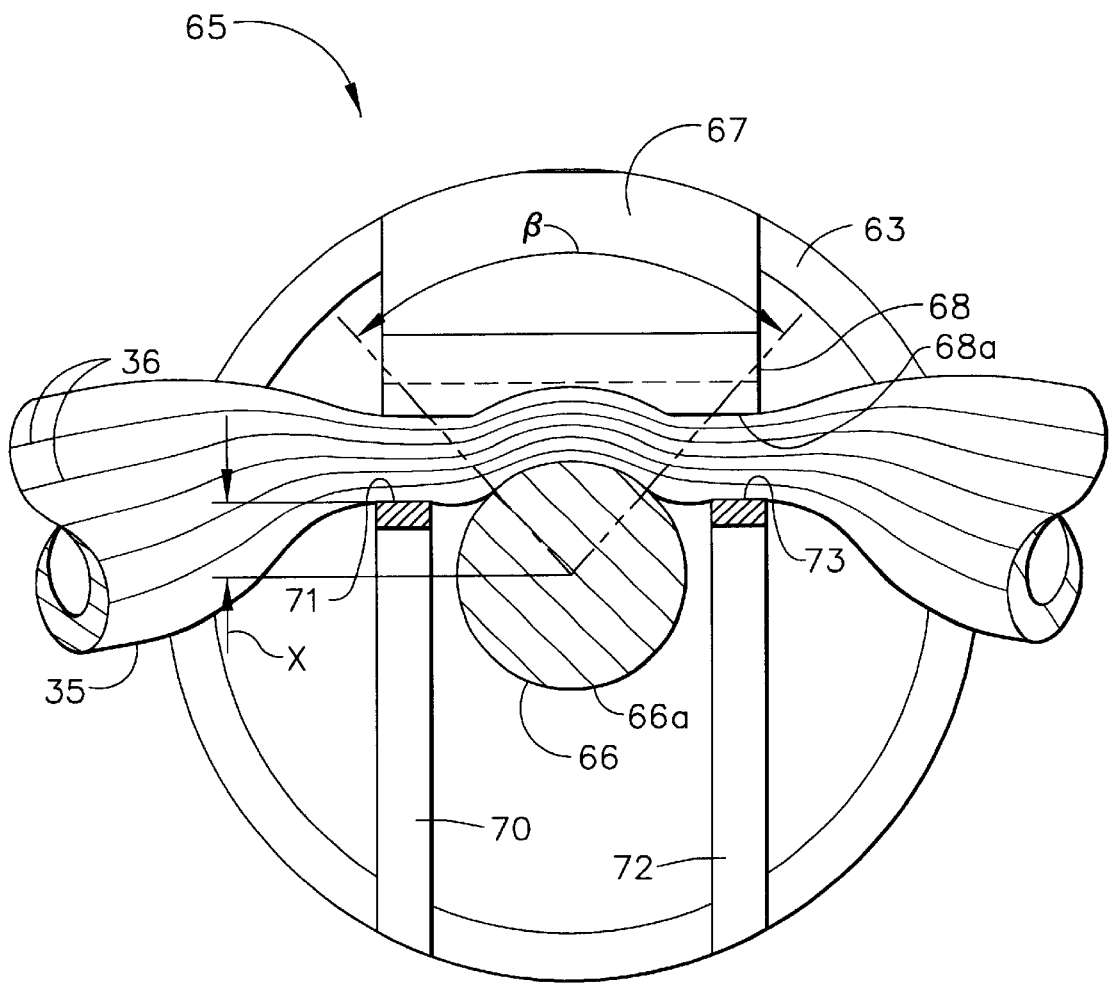
FIG. 8 is an enlarged cross sectional view of the distal end effector of the improved surgical instrument of FIG. 2, wherein the end effector has closed upon a vessel.

FIGS. 7–10 illustrate the end effector 65 according to the present invention which is illustrated in FIG. 2, its method of use, and the results obtained when an end effector 65 according to the present invention is used on tissue. The end effector 65 differs from the prior art instrument of FIG. 3 in that the first and second support surfaces 71,73 are provided to clamp the vessel 35 against the clamping surface 68a laterally on either side of ultrasonic blade 66. Tissue is also clamped between the clamping surface 68a and the ultrasonic blade 66. The first and second support surfaces 71,73 are inactive or ultrasonically isolated from the ultrasonic blade 66. FIG. 7 shows an isometric view of the end effector 65 of the present invention clamped upon a vessel 35 prior to the application of ultrasonic energy. FIG. 8 is a sectioned end view of the isometric view of FIG. 7 and used pressure streamlines 36 to show the areas of tissue compression. It is of note that the first and second support surfaces 71,73 of the present invention support the vessel 35 laterally on both sides of the ultrasonic blade 66, and this lateral support creates a wider angular compression zone β against the ultrasonic blade 66 than the prior art end effector 65a (see FIG. 4). As shown by the pressure streamlines 36, more of vessel 35 is compressed between the ultrasonic blade 66 and the clamping surface 68a. Further, the pressure streamlines show the compression on the tissue is substantially laterally continuous across the end effector 65. When the ultrasonic blade 66 is energized, the application of ultrasonic energy will produce a wider portion of compressed coagulated tissue i.e.: welded tissue.

Figure 9:
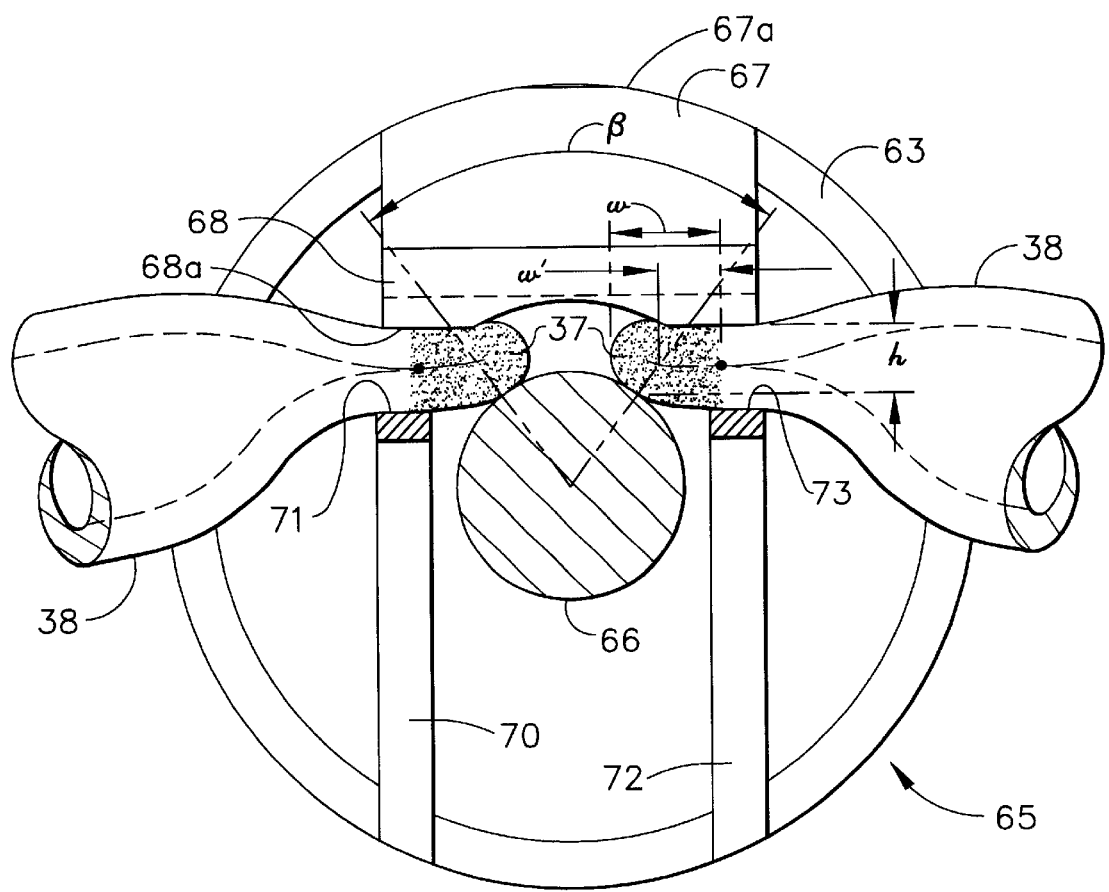
FIG. 9 is an enlarged cross sectional view of the distal end of the improved surgical instrument of FIG. 8 wherein the application of ultrasonic energy has coagulated and cut the vessel within the end effector and the severed vessels are clamped between the clamp arm and the first and second support beams.
Figure 10:
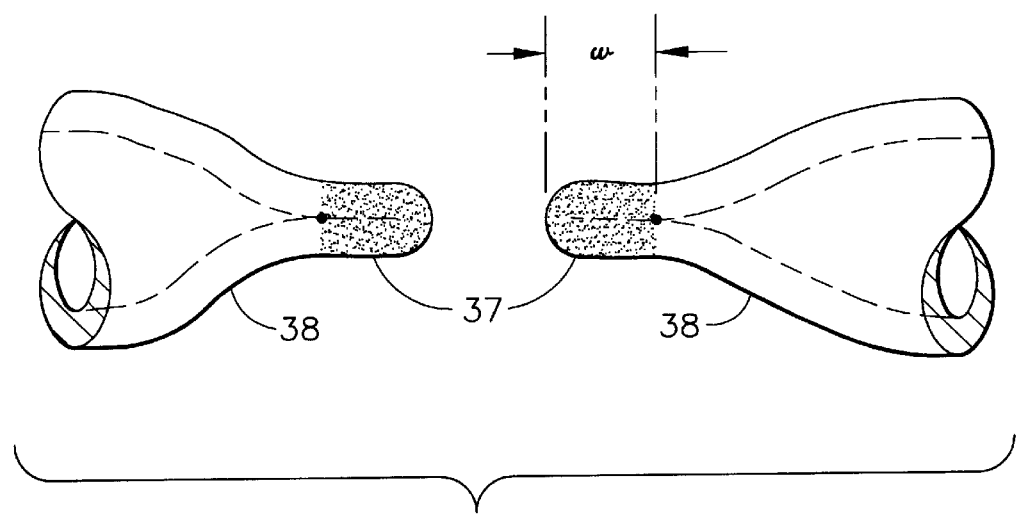
FIG. 10 is an enlarged view of the coagulated and cut vessel of FIG. 9, after release from the prior art surgical instrument, wherein the coagulated tissue is identified by stippling.

FIGS. 9 and 10 show the effects of the application of ultrasonic energy to the clamped vessel 35 of FIG. 8. In FIG. 9, the ultrasonic energy has welded and cut the compressed portion of vessel 35 into two preferred severed vessels 38. The preferred severed vessels 38 are welded at the ends and that the length of the welded tissue is designated by a welded tissue length " ". Note that the first and second support surfaces 71 and 73 of the present invention hold the majority of the preferred severed vessels 38 away from the ultrasonic blade 66 and that a portion of welded tissue is in contact with the ultrasonic blade 66. A large portion of the welded tissue length " " is formed outside of the angular compression zone β by lateral thermal spread. This portion of welded tissue is laterally spaced away from the ultrasonic blade 66 and is designated as length ' Preferred severed vessels 38 will remain clamped between the clamping surface 68a and the first and second support surfaces 71,73 until the clamp arm 67a is opened. It should be noted that the end effector 65 of the preferred invention compresses a laterally wider portion of tissue than the prior art end effector 65a and when energy is applied to this compressed tissue, produces a laterally longer tissue weld. This is shown by the wielded length ' of the present invention (FIG. 10) which is longer than the welded length "d" of the prior art invention (FIG. 6).

Therefore, the method of use of the present invention is to compress tissue against the side of the ultrasonic blade 66 and compress tissue laterally to the ultrasonic blade 66 to create a substantially continuous pressure region. Ultrasonic energy is applied to the tissue compressed against the ultrasonic blade 66 to create a tissue weld. Lateral thermal spread coagulates compressed tissue adjacent to and laterally spaced away from the ultrasonic blade 66. This increases the size or lateral width of the tissue weld by coagulating compressed tissue not in contact with the ultrasonic blade 66.

The first and second support beams 70,72 are preferably formed as an extension of the metallic outer sheath 63. It is also possible to construct first and second support beams 70, as a secondary piece or pieces that are fixably attached to the metallic outer sheath 63 (not shown). Forming the first and second support beams 70,72 from at least one secondary piece offers additional flexibility to the preferred instrument. If desired, first and second support beams 70,72 can be constructed from a thermally conducting material for the purpose of conducting heat away from the clamped tissue. This limits the flow of heat into the compressed tissue (from lateral thermal spread) and provides precise control of the lateral length of the tissue weld. A wide variety of thermally conducting materials are available such as stainless steel, iron, aluminum, copper, magnesium or any other thermally conductive material.

If desired, a thermally resistive material can be used in the construction of the first and second support beams 70,72. The thermally resistive material confines or channels the flow of heat (from lateral thermal spread) into the tissue compressed between the thermally resistive first and second support beams 70,72 and the clamping surface 68a. This channeling effect effectively maximizes the length of the tissue weld by exposing the maximum amount of compressed tissue to lateral thermal spread. First and second support beams 70,72 can be formed of thermally resistive materials such as thermoform or thermoset plastics, carbon-carbon or coated with thermally resistive materials such as ceramics.

Figure 11:
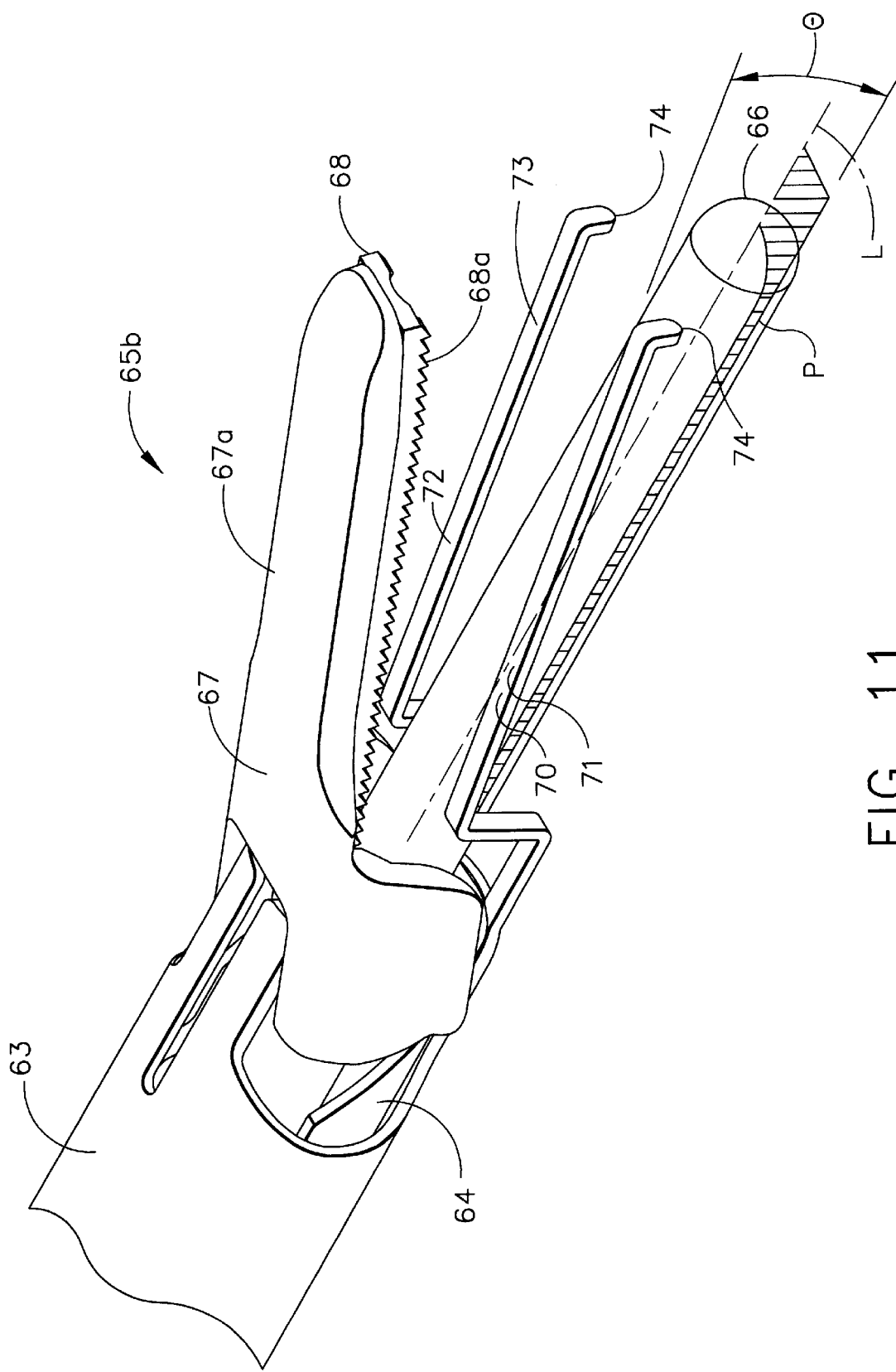
FIG. 11 is an enlarged cross sectional view of the distal end of an alternate embodiment of the improved surgical instrument of FIG. 2, showing the clamp arm in an open position and the first and a second support beams in an angled position.
Figure 14:
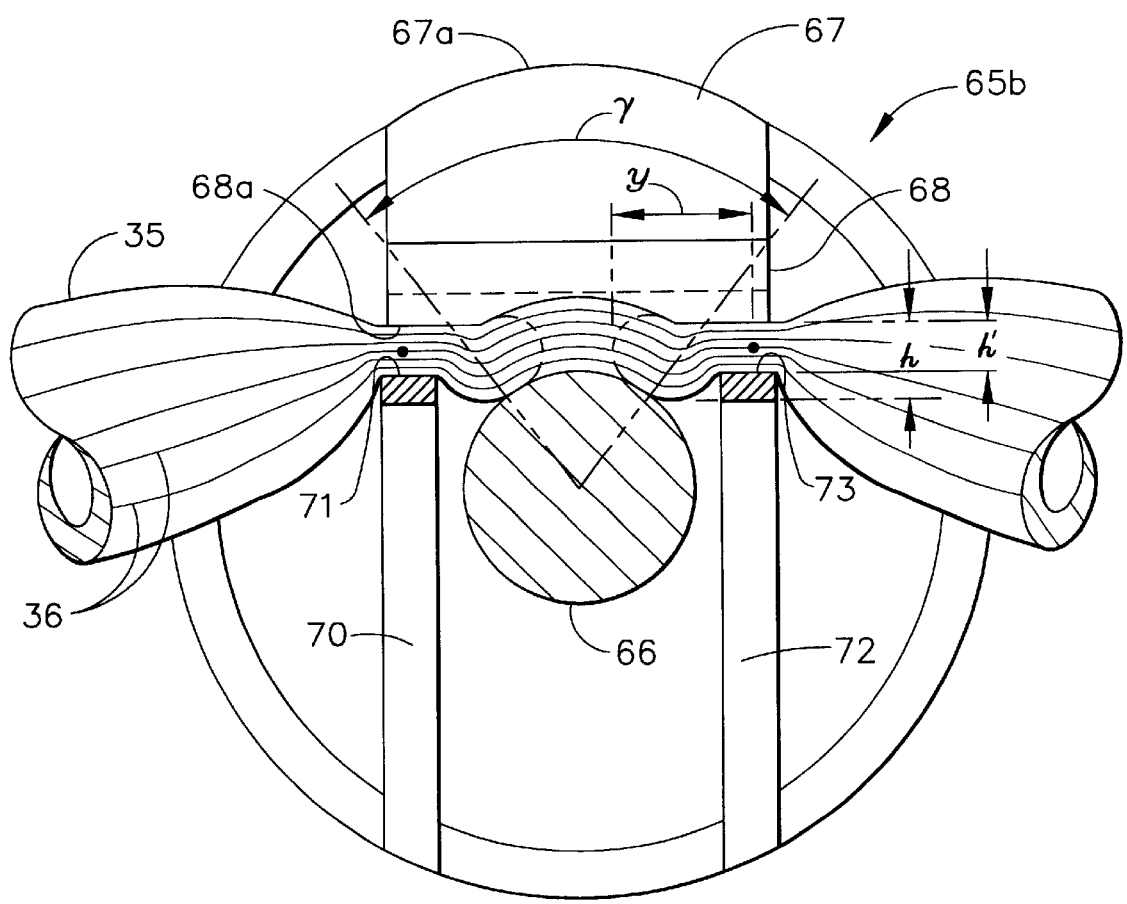
FIG. 14 is an enlarged cross sectional view of the improved surgical instrument of FIG. 13, showing the end effector arm in a fully closed position and the tissue portion clamped between the clamp arm and the blade prior to the application of ultrasonic energy.

Turning now to FIGS. 11–15, an alternate embodiment of the preferred invention is shown, along with its method of use. In this alternate embodiment, first and second support beams 70,72 and first and second support surfaces 71,73 are spaced away from and angled at a support surface angle "θ"

relative to a longitudinal axis "L" of the ultrasonic blade 66. FIG. 11 shows an isometric view of the end effector 65b with the clamp arm 67a in a fully open position. The first and second support surfaces 71,73 are shown angled upwards at the support surface angle "θ" relative to a longitudinal axis of the ultrasonic blade 66. A horizontal plane "P" is provided extending laterally away from the longitudinal axis of the ultrasonic blade 66 and support surface angle "θ" is measured between plane "P" and the first support surface 71. In this embodiment of FIG. 2, the first and second support beams 70,72 are a cantilever spring formed from a resilient material such as but not limited to stainless steel, and are designed to deflect downward as the clamp arm 67a closes. The additional deflection increases the clamping force on tissue such as vessel 35 (FIG. 14). The support surface angle "θ" may be between 3 degrees and 60 degrees and preferably is 10 degrees.

Figure 12:
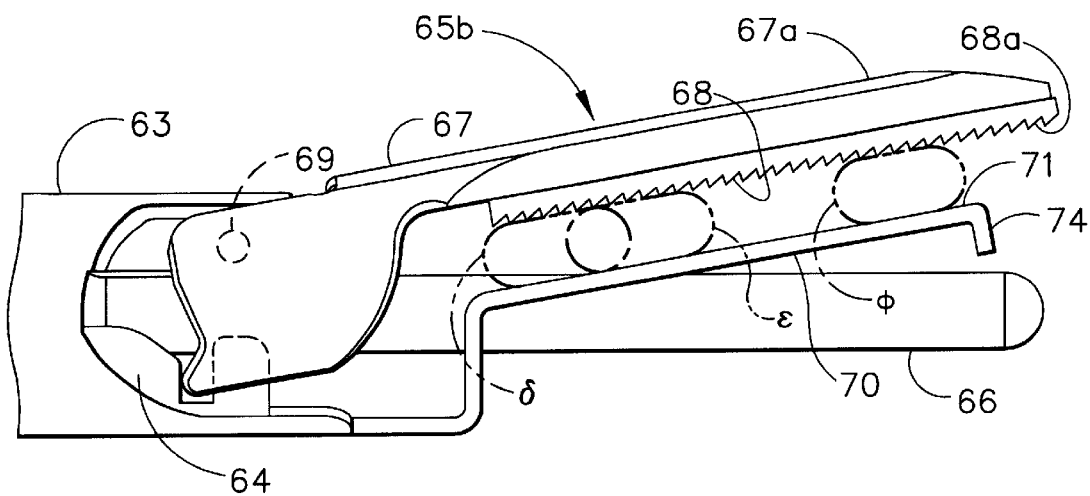
FIG. 12 is side elevational view of the distal end of the embodiment of the improved surgical instrument of FIG. 11, showing the end effector in a partially closed position and three possible tissue portion clamping locations within the end effector.
Figure 13:
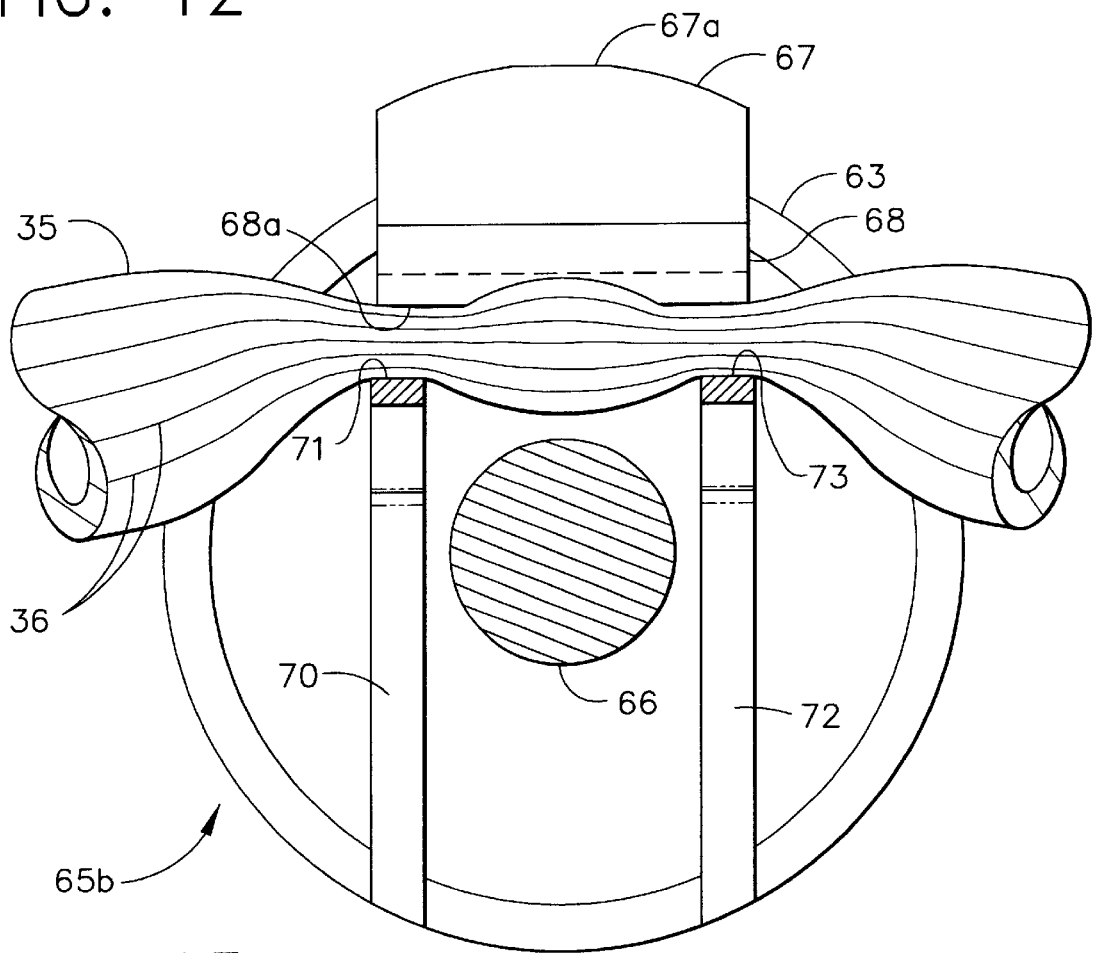
FIG. 13 is an enlarged cross sectional view of FIG. 12, wherein the end effector is shown partially closed upon a tissue portion at a distal end of the end effector and the tissue portion is clamped between the clamp arm and the first and second tissue support beams above the ultrasonic blade.

FIGS. 12 and 13 show the clamp arm 67a moved from the first open position of FIG. 11 to a second partially closed position to compress tissue. With the clamp arm 67a in the second position, it is possible to clamp tissue in three different locations within the end effector 65b. In all three cases, tissue is clamped against the clamping surface 68a and first and second tissue support surfaces 71 and 73, but in one of the locations, tissue is clamped spaced away from the ultrasonic blade 66. Thus, the end effector 65b of this embodiment has the ability to clamp tissue independently from the ultrasonic blade. In all cases, tissue must be clamped against the ultrasonic blade 66 to coagulate tissue. These three locations will now be described In the first location, herein designated a tissue location "δ", tissue is located proximally within the end effector 65 and is clamped between the first and second support surfaces 71,73, the ultrasonic blade 66, and clamping surface 68a. The tissue is held (at a support surface angle θ) against the ultrasonic blade 66. Actuation of the surgical instrument 23 will coagulate this tissue similarly to that described above in the preferred invention description.

A second location, designated a tissue location "ε", has tissue compressed between the clamping surface 68a, the first and second support surfaces 71,73 and the ultrasonic blade 66. The proximal end of the tissue is in contact with the ultrasonic blade 66 and the distal end of the tissue is suspended above the ultrasonic blade 66. At tissue location "ε", actuation of the surgical instrument 23 will coagulate and cut the tissue in a proximal to distal manner as the operator closes the clamp arm 67a against an active ultrasonic blade 66.

In the third location, designated as a tissue location "φ", the tissue or vessel 35 is compressed between the clamping surface 68a and the first and second support surfaces 71,73. At tissue location "φ", the tissue portion is held suspended above the ultrasonic blade 66. An end view of clamped tissue is shown in FIG. 13 to better show how the vessel 35 is held suspended above the ultrasonic blade 66. Pressure streamlines 36 are provided to show areas of clamping pressure. From this position, the vessel 35 can be brought down upon an active or an un-active ultrasonic blade 66 when the clamp arm 67a is moved to the fully closed position (FIGS. 2 and 14).

Figure 15:
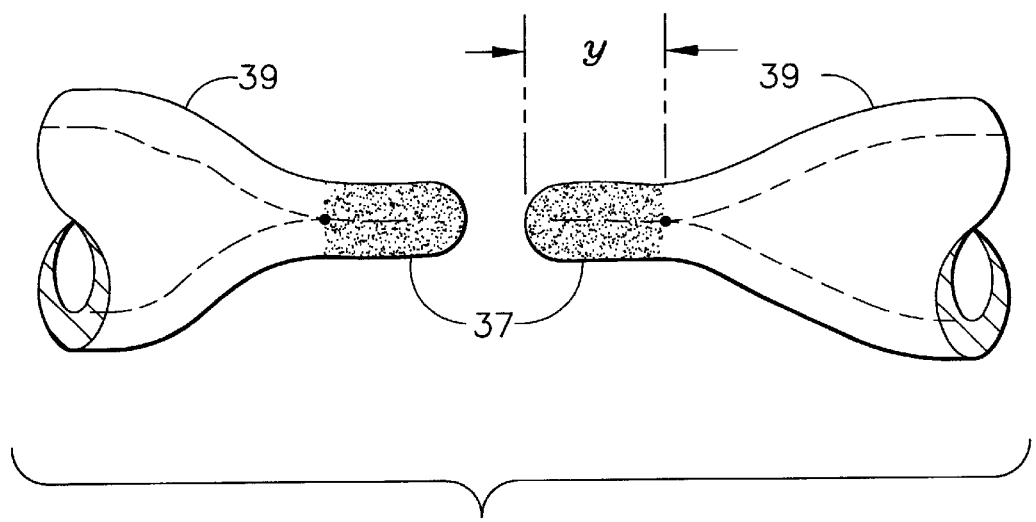
FIG. 15 is an enlarged view of the vessel of FIG. 14, wherein the vessel has been coagulated and cut and released from the end effector, and the coagulated tissue is identified by stippling.

As the clamp arm 67a moves to the fully closed position of FIG. 14, first and second support beams 70,72 deflect downward to the horizontal position as shown. In FIG. 14, vessel 35 in is held against ultrasonic blade 66 prior to the application of ultrasonic energy. The additional deflection of the first and second support beams 70,72 increases the pressure on the vessel 35 over the previously described instrument of FIGS. 2 and 7–10 which compresses tissue to a height of "h" (see FIGS. 9 and 14). This additional deflection compresses the portion of the vessel 35 clamped between the clamping surface 68 and the first and second support surface 71,73 an additional amount to a second clamped height "h'". The reader is advised to note that the second clamped tissue height "h'" of FIG. 14 is less than the first clamped height "h" of FIG. 9 due to the increased clamping forces exerted by the first and second support beams 70,72. This increase in clamping force results in a slight bulging of the vessel 35 between each of the first and second support beams 70,72 and the ultrasonic blade 66. The additional compression from the angled support beams 71,73 bulges the tissue inwardly towards the ultrasonic blade 66 and creates an angular compression zone "γ" that is slightly wider than the angular compression zone "β" as shown in FIGS. 8 and 9. The application of ultrasonic energy to the compressed vessel 35 welds and cuts the vessel 35 producing the alternate severed vessels 39 as shown in FIG. 15. The coagulated tissue 37 on the ends of the severed vessels 35a forms a welded tissue length "y". The cut ends of the alternate severed vessels 39 are shown as dashed lines in FIG. 14. The continued application of ultrasonic energy will cut the vessel 35, and a first portion of the vessel is in contact with the ultrasonic blade 66 and a second portion compressed against the tissue support surfaces 71,73. The continued application of ultrasonic energy to the clamped vessel 35 coagulates and severs the vessel 35 by coagulating and atomizing or pluming the tissue.

The method of use of the alternate embodiment of the present invention is to compress a portion of uncompressed tissue between the clamping surface 68a and the first and second support surfaces 71,73. This creates a pressure region having a central uncompressed tissue region located between the first and second support surfaces 71,73. This uncompressed tissue can, as described above, be in contact with or spaced away from the ultrasonic blade 66. The tissue portion is moved to bring all of the uncompressed tissue portion between the first and second support surfaces 71,73 into contact with an ultrasonic energy source i.e.: ultrasonic blade 66. This contact creates a substantially continuous pressure region within the tissue portion clamped within end effector 65b. Ultrasonic energy is applied to the compressed tissue in contact with the ultrasonic blade 66 to create a tissue weld. Lateral thermal spread increases the width or size of the tissue weld in compressed tissue by spreading the weld laterally away from the compressed tissue in contact with the ultrasonic blade 66. The tissue weld spreads into compressed tissue adjacent to and laterally spaced away from the ultrasonic blade 66. Continued application of ultrasonic energy cuts the welded tissue.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical method for increasing the size of a tissue weld in clamped tissue, comprising the steps of:
   a) providing an end effector for an ultrasonic surgical instrument, said end effector including:
      i) an ultrasonic blade having a proximal and a distal end;

ii) a clamping mechanism having a clamping surface positioned opposite said ultrasonic blade, wherein said clamping mechanism is adapted to clamp tissue against a side of said ultrasonic blade;

iii) a first support surface positioned laterally on a first side of said ultrasonic blade, said first support surface being ultrasonically isolated from said blade and positioned opposite at least a portion of said clamping surface; and iv) a second support surface positioned laterally on a second side of said ultrasonic blade, said second support surface being ultrasonically isolated from said blade and positioned opposite at least a portion of said clamping surface;

b) actuating said clamping mechanism to clamp tissue between said clamping surface and said ultrasonic blade, and between said clamping surface and said first and second tissue support surfaces, the clamped tissue defining a substantially continuous pressure region; and c) applying ultrasonic energy to said ultrasonic blade for the creation of a tissue weld in the substantially continuous pressure region, the tissue weld spreading from tissue clamped between said clamping surface and said ultrasonic blade and into tissue clamped between said clamping surface and said first and second tissue support surfaces.

2. The method of claim 1, the method further comprising cutting said tissue weld.

3. The method of claim 1 wherein said ultrasonic energy is applied at a frequency between 20 kHz to 250 kHz.

4. The method of claim 3 wherein said ultrasonic energy is applied at a frequency of 55 kHz.

5. The method of claim 1 wherein said ultrasonic energy is applied with a side of said ultrasonic blade, said side located between said proximal and distal end of said ultrasonic blade.

6. A surgical method for increasing the size of a tissue weld in compressed tissue comprising the steps of:

a) providing an end effector for an ultrasonic surgical instrument, said end effector including;
  i) an ultrasonic blade having a proximal and a distal and;
  ii) a clamping mechanism having a clamping surface positioned opposite said ultrasonic blade, wherein said clamping mechanism is adapted to clamp tissue against said ultrasonic blade;
  iii) a first support surface positioned laterally on a first side of said ultrasonic blade, said first support surface being ultrasonically isolated from said blade and positioned opposite at least a portion of said clamping surface, said first support surface having a support surface angle relative to the longitudinal axis of said ultrasonic blade; and
  iv) a second support surface positioned laterally on a second side of said ultrasonic blade, said second support surface being ultrasonically isolated from said blade and positioned opposite at least a portion of said clamping surface, said second support surface having generally the same support surface angle as said first support surface;

b) moving said clamping mechanism to a first position to clamp tissue between said clamping surface and said first and second support surfaces, said clamped tissue spaced away from said ultrasonic blade and having an uncompressed tissue region positioned opposite said blade;

c) moving said clamping mechanism to a second position to clamp the uncompressed tissue region against said ultrasonic blade to create a substantially continuous pressure region within the tissue clamped within said end effector; and d) applying ultrasonic energy to the clamped tissue in contact with said ultrasonic blade to create a tissue weld, the tissue weld spreading away from the clamped tissue in contact with said ultrasonic blade and into clamped tissue adjacent to and spaced away from said ultrasonic blade.

7. The method of claim 6, the method further comprising cutting said tissue weld.

8. The method of claim 6 wherein said ultrasonic energy is applied at a frequency between 20 kHz to 250 kHz.

9. The method of claim 8 wherein said ultrasonic energy is applied at a frequency of 55 kHz.

10. The method of claim 6 wherein said ultrasonic energy is applied with a side of said ultrasonic blade, said side between said proximal and distal end.

11. The method of claim 10 wherein said support surface angle is between about one degree and sixty degrees.

12. The method of claim 11 wherein said support surface angle is preferably ten degrees.

13. A surgical method for increasing the size of a tissue weld in compressed tissue, comprising the steps of:

a) providing an end effector for an ultrasonic surgical instrument, said end effector including;
  i) an ultrasonic blade having a proximal and a distal end;
  ii) a clamping mechanism having a clamping surface positioned opposite said ultrasonic blade, wherein said clamping mechanism is adapted to clamp tissue against said ultrasonic blade;
  iii) a first support surface positioned laterally on a first side of said ultrasonic blade, said first support surface being ultrasonically isolated from said blade and positioned opposite at least a portion of said clamping surface, said first support surface having a support surface angle relative to the longitudinal axis of said ultrasonic blade; and
  iv) a second support surface positioned laterally on a second side of said ultrasonic blade, said second support surface being ultrasonically isolated from said blade and positioned opposite at least a portion of said clamping surface, said second support surface having generally the same support surface angle as said first support surface;

b) moving said clamping mechanism to a first position to clamp tissue between said clamping surface and said first and second support surfaces, the clamped tissue spaced away from said ultrasonic blade and the tissue having an uncompressed tissue region opposite said blade, c) activating said ultrasonic blade; and d) moving said clamping mechanism to a second position to clamp tissue against said active ultrasonic blade to create a tissue weld within the substantially continuous pressure region.

14. The method of claim 13, the method further comprising cutting said tissue weld.

15. The method of claim 13 wherein said ultrasonic energy is applied at a frequency between 20 kHz to 250 kHz.

16. The method of claim 15 wherein said ultrasonic energy is applied at a frequency of 55 kHz.

17. The method of claim 13 wherein said ultrasonic energy is applied with a side of said ultrasonic blade, said side between said proximal and distal end.

18. The method of claim 13 wherein said support surface angle is between about one degree and sixty degrees.

19. The method of claim 18 wherein said support surface angle is preferably ten degrees.

* * * * *